(12) United States Patent
Kemp

(10) Patent No.: US 12,076,540 B2
(45) Date of Patent: *Sep. 3, 2024

(54) AUTOINJECTOR

(71) Applicant: SANOFI-AVENTIS DEUTSCHLAND GMBH, Frankfurt am Main (DE)

(72) Inventor: Thomas Kemp, Ashwell (GB)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 205 days.

This patent is subject to a terminal disclaimer.

(21) Appl. No.: 17/586,272

(22) Filed: Jan. 27, 2022

(65) Prior Publication Data

US 2022/0143322 A1 May 12, 2022

Related U.S. Application Data

(60) Continuation of application No. 16/721,467, filed on Dec. 19, 2019, now Pat. No. 11,260,181, which is a
(Continued)

(30) Foreign Application Priority Data

Jul. 9, 2013 (EP) .................................... 13175661

(51) Int. Cl.
*A61M 5/315* (2006.01)
*A61M 5/20* (2006.01)
(Continued)

(52) U.S. Cl.
CPC ...... *A61M 5/31586* (2013.01); *A61M 5/2033* (2013.01); *A61M 5/3202* (2013.01);
(Continued)

(58) Field of Classification Search
CPC ............ A61M 5/31586; A61M 5/2033; A61M 5/3202; A61M 5/326; A61M 5/5086;
(Continued)

(56) References Cited

U.S. PATENT DOCUMENTS

| 5,762,646 A | 6/1998 | Cotter |
| 7,597,685 B2 | 10/2009 | Olson |

(Continued)

FOREIGN PATENT DOCUMENTS

| CN | 101983079 | 3/2011 |
| CN | 102149419 | 8/2011 |

(Continued)

OTHER PUBLICATIONS

Extended European Search Report in Application No. 13175661.1, dated Jan. 3, 2014, 7 pages.

(Continued)

*Primary Examiner* — Theodore J Stigell
(74) *Attorney, Agent, or Firm* — Fish & Richardson P.C.

(57) ABSTRACT

An autoinjector includes a case adapted to hold a medicament container having a needle, a needle shroud slidably disposed in the case and translatable between an extended position relative to the case in which the needle is covered and a retracted position relative to the case in which the needle is exposed, and a plunger slidably disposed in the case. The case includes a rib. The plunger includes a plunger boss adapted to abut the rib and the needle shroud when the needle shroud is in the extended position and disengage the rib when the needle shroud is in the retracted position to allow the plunger to translate axially relative to the case.

20 Claims, 12 Drawing Sheets

Related U.S. Application Data division of application No. 14/903,398, filed as application No. PCT/EP2014/064424 on Jul. 7, 2014, now Pat. No. 10,525,206.

(51) Int. Cl.
*A61M 5/32* (2006.01)
*A61M 5/50* (2006.01)

(52) U.S. Cl.
CPC ............... *A61M 2005/2013* (2013.01); *A61M 2005/3247* (2013.01); *A61M 5/326* (2013.01); *A61M 5/5086* (2013.01); *A61M 2205/581* (2013.01); *A61M 2205/582* (2013.01); *A61M 2205/583* (2013.01)

(58) Field of Classification Search
CPC .. A61M 2005/2013; A61M 2005/3247; A61M 2205/581; A61M 2205/582; A61M 2205/583; A61M 5/20
See application file for complete search history.

(56) References Cited

U.S. PATENT DOCUMENTS

| | | | |
|---|---|---|---|
| 8,308,695 | B2 | 11/2012 | Laiosa |
| 8,496,619 | B2 | 7/2013 | Kramer et al. |
| 8,702,655 | B2 | 4/2014 | Chong et al. |
| 9,199,038 | B2 | 12/2015 | Daniel |
| 9,220,847 | B2 | 12/2015 | Holmqvist et al. |
| 9,364,610 | B2 | 6/2016 | KraMer et al. |
| 9,364,611 | B2 | 6/2016 | KraMer et al. |
| 9,408,976 | B2 | 8/2016 | Olson et al. |
| 9,446,195 | B2 | 9/2016 | Kramer et al. |
| 9,468,722 | B2 | 10/2016 | Olson |
| 9,480,798 | B2 | 11/2016 | Karisson et al. |
| 10,525,206 | B2 * | 1/2020 | Kemp ................. A61M 5/2033 |
| 2010/0185178 | A1 | 7/2010 | Sharp et al. |
| 2011/0054414 | A1 | 3/2011 | Shang et al. |
| 2011/0092915 | A1 | 4/2011 | Olson et al. |
| 2011/0196339 | A1 | 8/2011 | Hirschel et al. |

FOREIGN PATENT DOCUMENTS

| | | |
|---|---|---|
| EP | 2399627 | 12/2011 |
| EP | 2399633 | * 12/2011 |
| EP | 2606924 | 6/2013 |
| JP | 2014-527894 | 10/2014 |
| RU | 2011148399 | 6/2013 |
| WO | WO 2008/059385 | 5/2008 |
| WO | WO 2010/017650 | 2/2010 |
| WO | WO 2011/101383 | 8/2011 |
| WO | WO 2012/122643 | 9/2012 |
| WO | WO 2013/034651 | 3/2013 |
| WO | WO 2013/048310 | 4/2013 |

OTHER PUBLICATIONS

International Preliminary Report on Patentability in International Application No. PCT/EP2014/064424, issued Jan. 12, 2016, 8 pages.

International Search Report and Written Opinion in International Application No. PCT/EP2014/064424, mailed Nov. 5, 2014, 11 pages.

* cited by examiner

AUTOINJECTOR

CROSS-REFERENCE TO RELATED APPLICATIONS

This application is a continuation of U.S. application Ser. No. 16/721,467, filed on Dec. 19, 2019, which is a divisional of application U.S. application Ser. No. 14/903,398, filed on Jan. 7, 2016, which is a U.S. national stage application under 35 USC § 371 of International Application No. PCT/EP2014/064424, filed on Jul. 7, 2014, which claims priority to European Patent Application No. 13175661.1, filed on Jul. 9, 2013, the entire contents of which are incorporated herein by reference.

TECHNICAL FIELD

This disclosure relates to an autoinjector.

BACKGROUND

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

There remains a need for an improved autoinjector.

SUMMARY

It is an object of the present invention to provide an improved autoinjector.

In an exemplary embodiment, an autoinjector according to some aspects of the present invention comprises a case adapted to hold a medicament container having a needle and the case including a rib, a needle shroud slidably disposed in the case and translatable between an extended position relative to the case in which the needle is covered and a retracted position relative to the case in which the needle (4) is exposed, and a plunger slidably disposed in the case. The plunger including a plunger boss adapted to abut the rib and the needle shroud when the needle shroud is in the extended position and disengage the rib when the needle shroud is in the retracted position to allow the plunger to translate axially relative to the case.

In an exemplary embodiment, a first shroud boss on the needle shroud abuts the plunger boss when the needle shroud is in the extended position. A second shroud boss on the needle shroud proximal of the first shroud boss abuts the plunger boss when the needle shroud is in the extended position. A resistance element is formed on the first shroud boss. The resistance element is adapted to engage the plunger boss as the needle shroud translates from the extended position to the retracted position. The resistance element includes at least one of a bump, a ramp, an abutment, a recess, a spring detent and a preloaded beam.

In an exemplary embodiment, a resilient shroud beam on the needle shroud is deflected by a resilient case backstop beam when the needle shroud translates from the retracted position to a second extended position distal relative to the case of the extended position. The resilient shroud beam abuts the resilient case backstop beam when the needle shroud is in the second extended position to prevent proximal movement of the needle shroud relative to the case. The resilient case backstop beam abuts the medicament container when the needle shroud is in the second extended position.

In an exemplary embodiment, the autoinjector further comprises a shroud spring biasing the needle shroud toward the extended position.

In an exemplary embodiment, the autoinjector further comprises a drive spring biasing the plunger relative to the case.

In an exemplary embodiment, the case includes a bayonet slot adapted to engage the plunger boss. The plunger boss partially disengages the bayonet slot when the plunger boss abuts the rib.

In an exemplary embodiment, the rib is angled with respect to a longitudinal axis of the case and imparts a rotational and an axial force on the plunger boss.

In an exemplary embodiment, the case includes a viewing window.

In an exemplary embodiment, the autoinjector further comprises a cap coupled to a protective needle sheath covering the needle.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Certain aspect of the present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
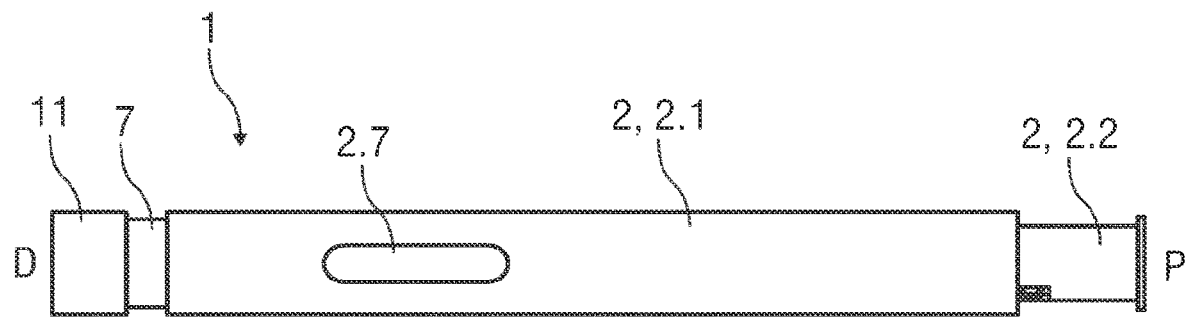
FIG. 1A is a side view of an exemplary embodiment of an autoinjector according to some aspects of the present invention during assembly.
Figure 1B:
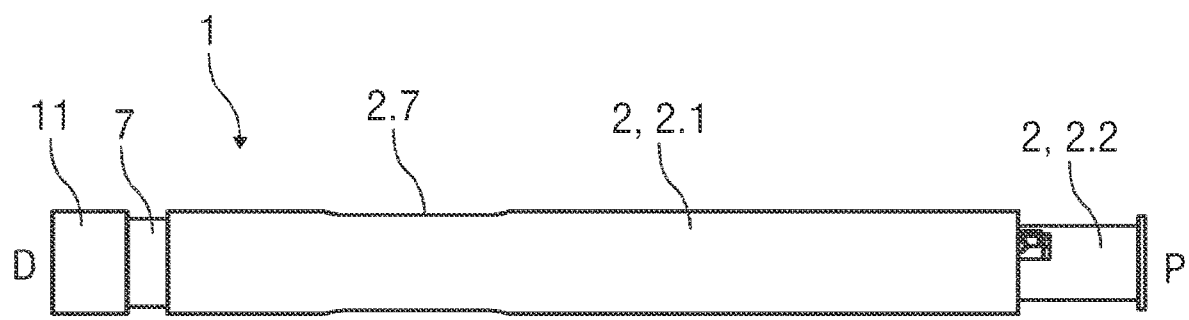
FIG. 1B is a side view of an exemplary embodiment of an autoinjector according to certain aspects of the present invention during assembly.

FIGS. 1A-D show an exemplary embodiment of an autoinjector 1 according to some aspects of the present invention during assembly. Referring to FIGS. 1A and 1B, an exemplary embodiment of the autoinjector 1 comprises a case 2 comprising a front case 2.1 and a rear case 2.2. In another exemplary embodiment, the case 2 may comprise a single case. A cap 11 may be removably coupled to a distal end of the case 2. The case 2 may include a viewing window 2.7, which may be a transparent portion of the case 2 or a cut-out. A needle shroud 7 may be telescoped within the case 2.

Figure 1C:
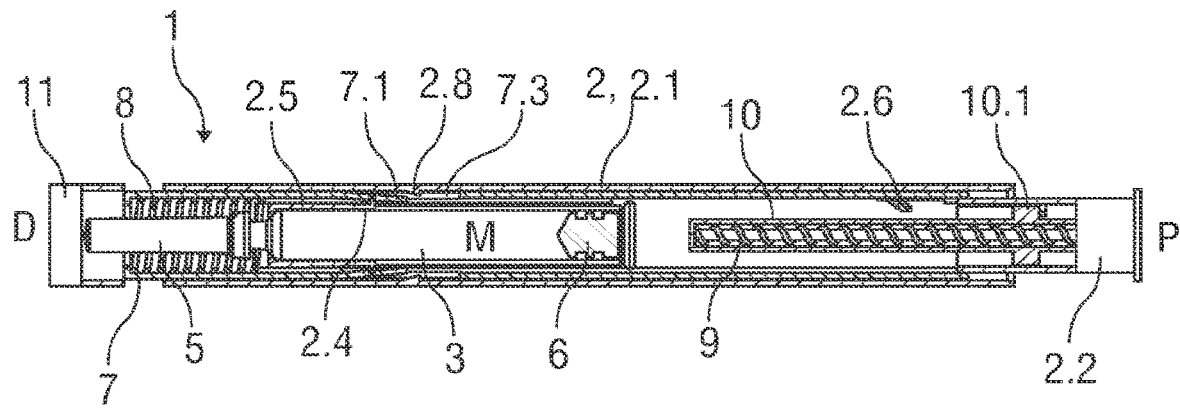
FIG. 1C is a longitudinal section of an exemplary embodiment of an autoinjector according to certain aspects of the present invention during assembly.
Figure 1D:
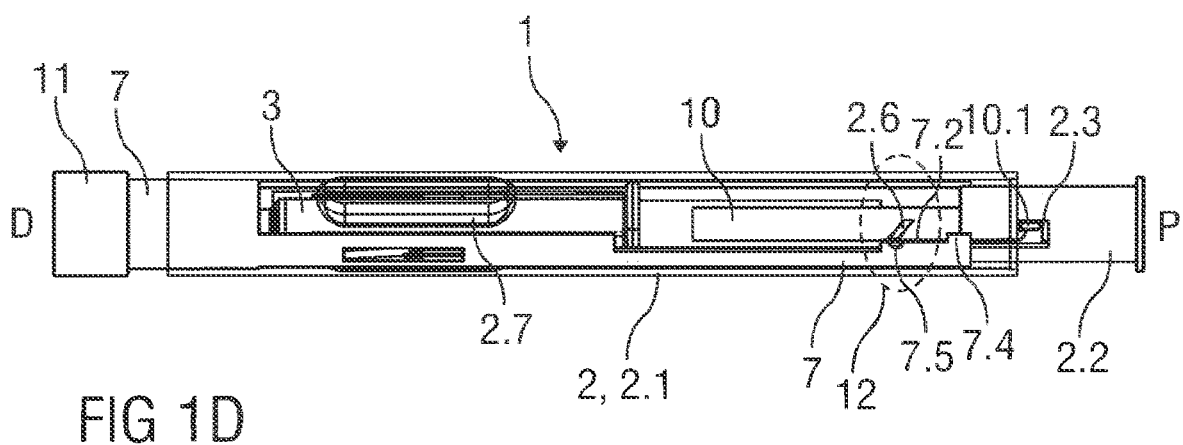
FIG. 1D is a semitransparent side view of an exemplary embodiment of an autoinjector according to certain aspects of the present invention during assembly.
Figure 3A:
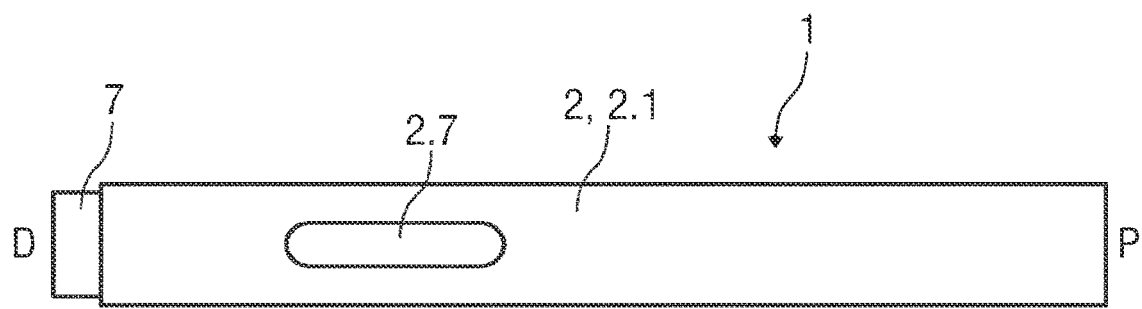
FIG. 3A is a side view of an exemplary embodiment of an autoinjector according to certain aspects of the present invention during use.
Figure 3B:
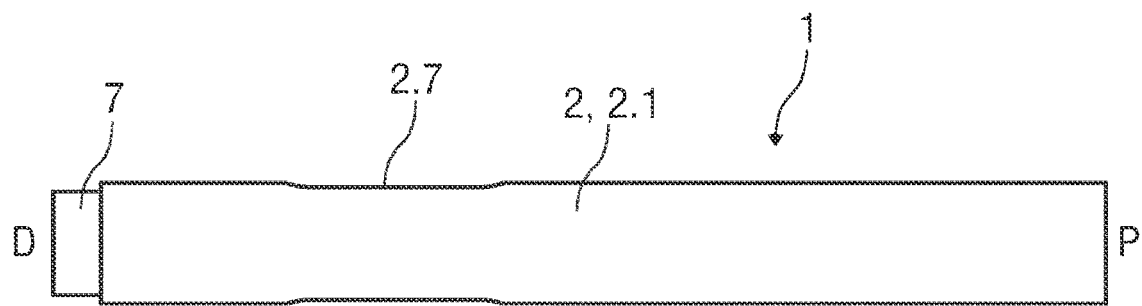
FIG. 3B is a side view of an exemplary embodiment of an autoinjector according to certain aspects of the present invention during use.
Figure 3C:
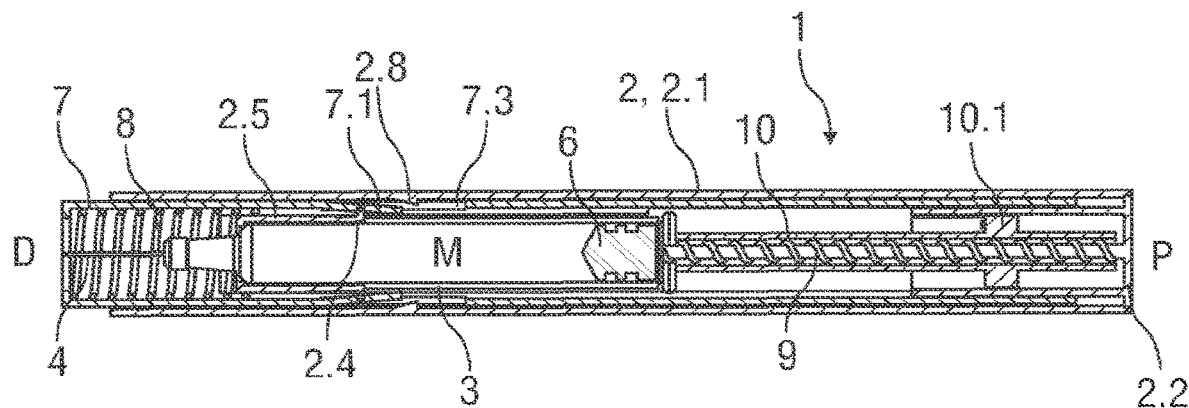
FIG. 3C is a longitudinal section of an exemplary embodiment of an autoinjector according to certain aspects of the present invention during use.
Figure 3D:
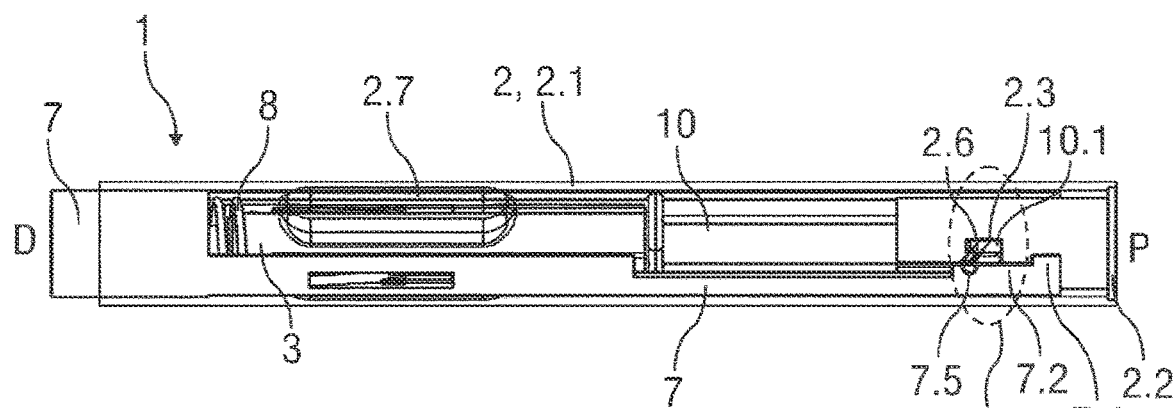
FIG. 3D is a semitransparent side view of an exemplary embodiment of an autoinjector according to certain aspects of the present invention during use.
Figure 4A:
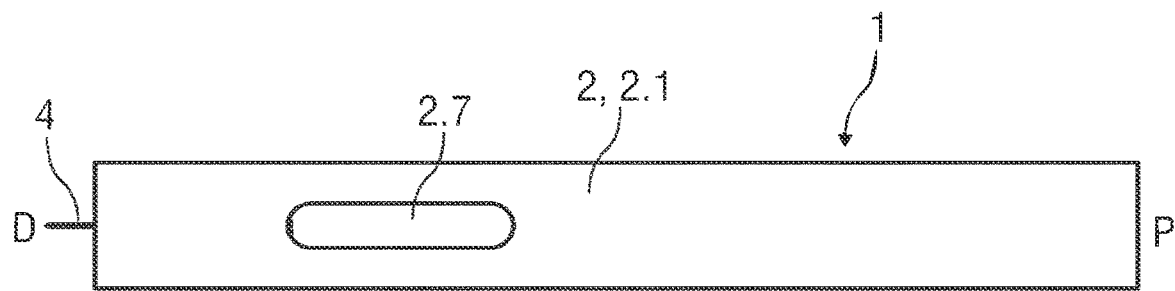
FIG. 4A is a side view of an exemplary embodiment of an autoinjector according to certain aspects of the present invention during use.
Figure 4B:
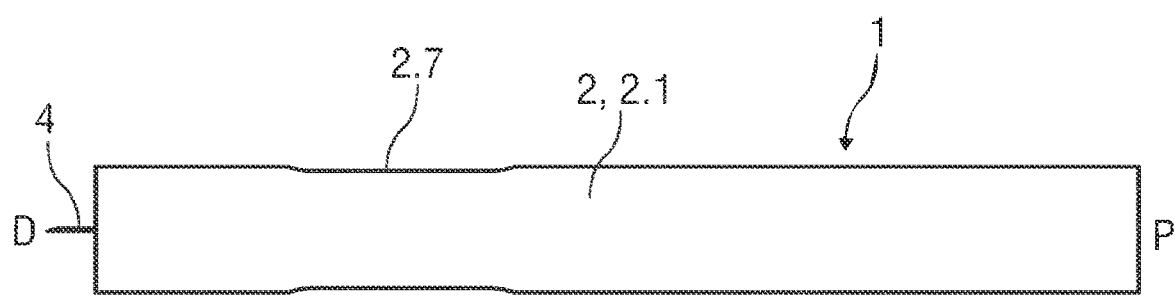
FIG. 4B is a side view of an exemplary embodiment of an autoinjector according to certain aspects of the present invention during use.
Figure 4C:
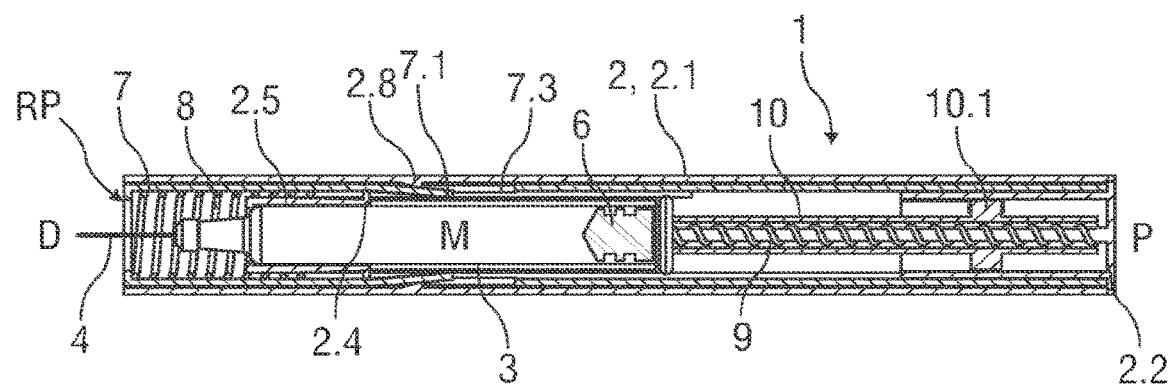
FIG. 4C is a longitudinal section of an exemplary embodiment of an autoinjector according to certain aspects of the present invention during use.
Figure 4D:
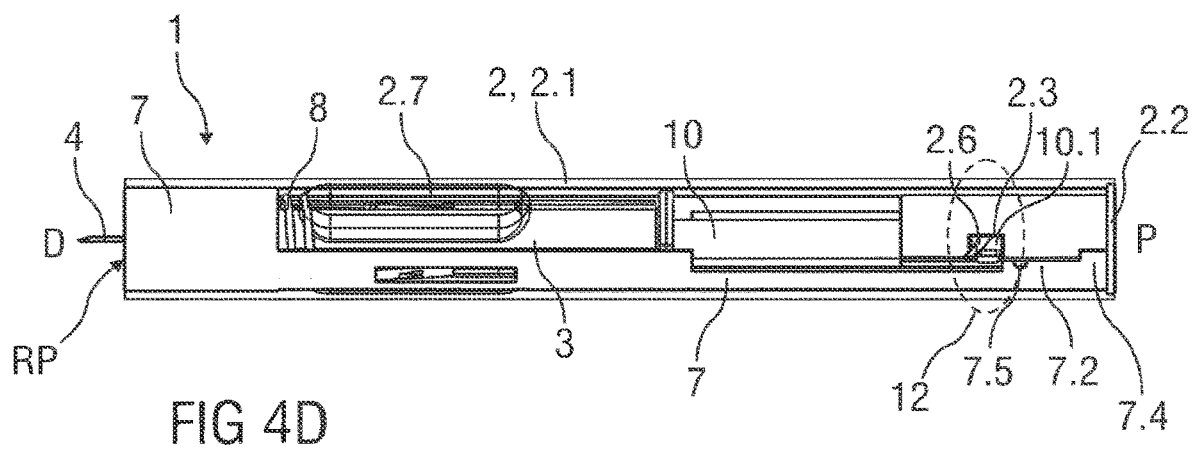
FIG. 4D is a semitransparent side view of an exemplary embodiment of an autoinjector according to certain aspects of the present invention during use.
Figure 5A:
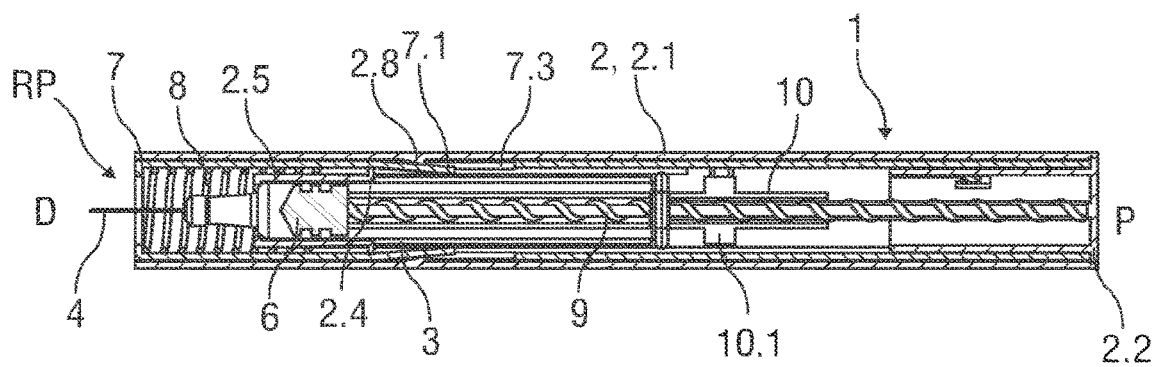
FIG. 5A is a longitudinal section of an exemplary embodiment of an autoinjector according to certain aspects of the present invention during use.
Figure 5B:
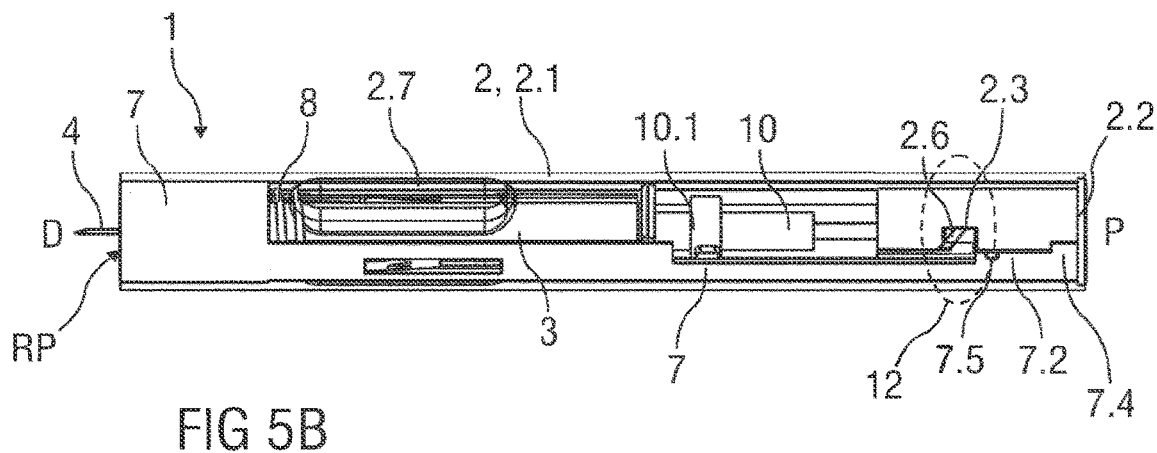
FIG. 5B is a semitransparent side view of an exemplary embodiment of an autoinjector according to certain aspects of the present invention during use.
Figure 6A:
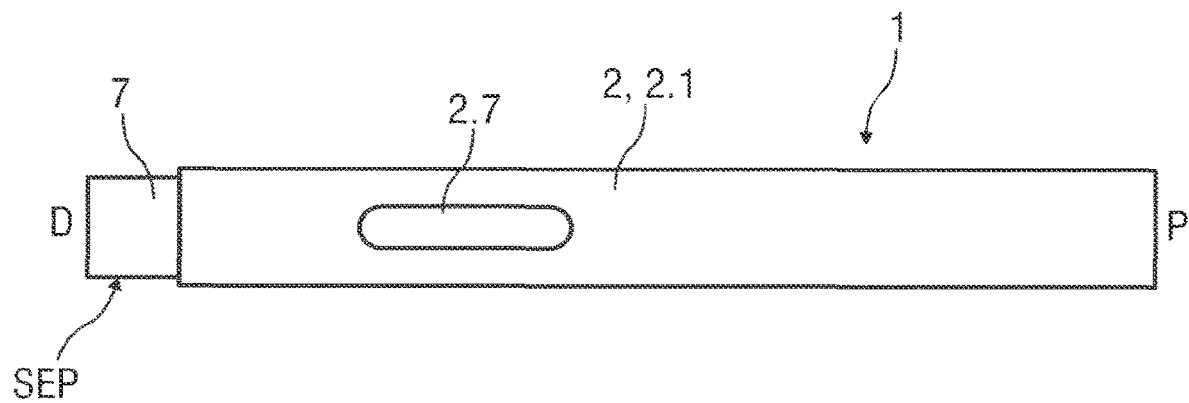
FIG. 6A is a side view of an exemplary embodiment of an autoinjector according to certain aspects of the present invention after use.
Figure 6B:
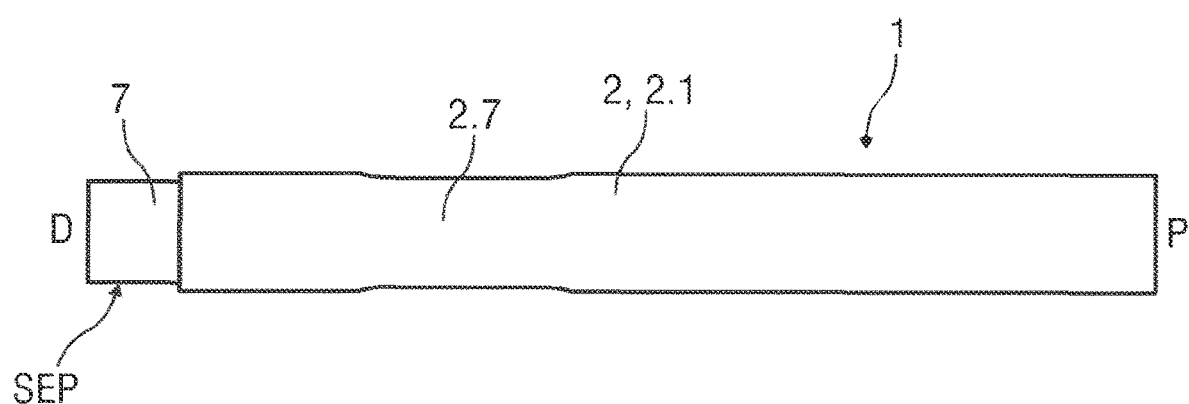
FIG. 6B is a side view of an exemplary embodiment of an autoinjector according to certain aspects of the present invention after use.
Figure 6C:
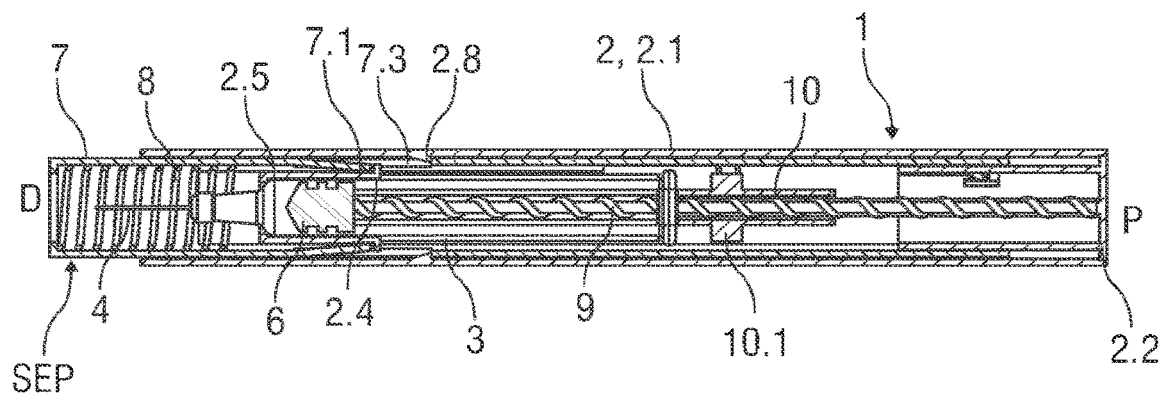
FIG. 6C is a longitudinal section of an exemplary embodiment of an autoinjector according to certain aspects of the present invention after use.
Figure 6D:
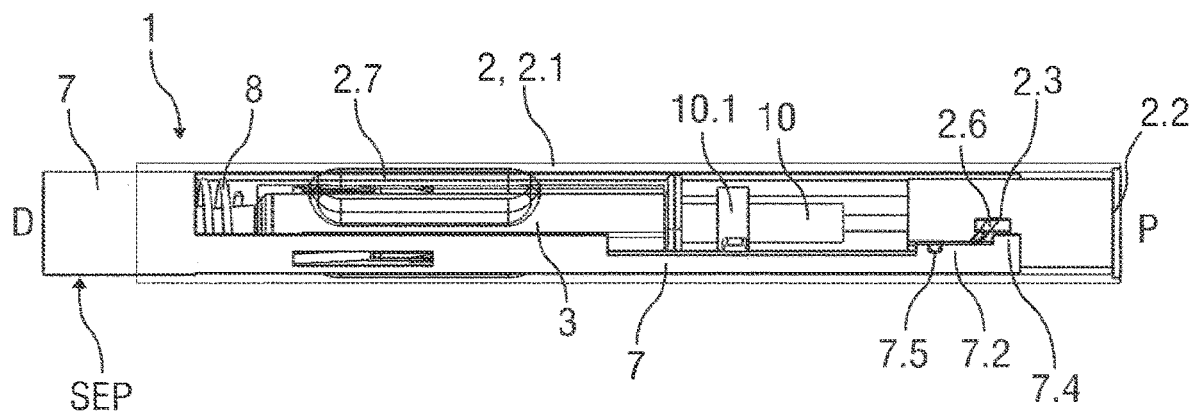
FIG. 6D is a semitransparent side view of an exemplary embodiment of an autoinjector according to certain aspects of the present invention after use.
Figure 7:
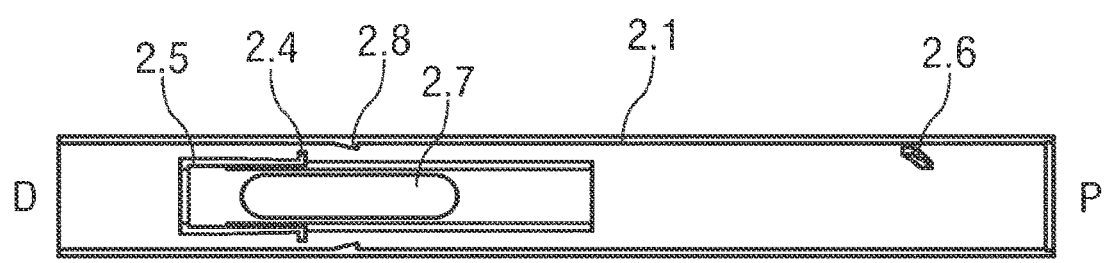
FIG. 7 is a longitudinal section of an autoinjector according to certain aspects of the present invention.

As shown in FIG. 1C, the case 2 is adapted to hold a medicament container, such as a syringe 3. The syringe 3 may be a pre-filled syringe and have a needle 4 (cf. FIG. 3C) arranged at a distal end. When the autoinjector 1 and/or the syringe 3 is assembled, a protective needle sheath 5 may be removably coupled to the needle 4. A stopper 6 is arranged for sealing the syringe 3 proximally and for displacing a medicament M contained in the syringe 3 through the needle 4. The syringe 3 is held in a fixed position relative to the case 2 and supported at its proximal end therein. In other exemplary embodiments, the medicament container may be a cartridge which includes the medicament M and engages a removable needle.

In an exemplary embodiment, the needle shroud 7 is slidably disposed in the case 2 and capable of moving proximally and distally relative to the case 2. The needle shroud 7 may be biased in the distal direction D relative to the case 2 by a shroud spring 8.

In an exemplary embodiment, a drive spring 9 (e.g., a compression spring) is arranged within a proximal part of the case 2. A plunger 10 serves for forwarding a force of the drive spring 9 to the stopper 6. In an exemplary embodiment, the plunger 10 is hollow and the drive spring 9 is arranged within the plunger 10 biasing the plunger 10 in the distal direction D against the rear case 2.2. In an exemplary embodiment, the plunger 10 comprises a plunger boss 10.1 being part of a plunger release mechanism 12 arranged for preventing release of the plunger 10 prior to depression of the needle shroud 7 against an injection site and for releasing the plunger 10 once the needle shroud 7 is depressed.

In an exemplary embodiment of a process for assembling the autoinjector 1, the drive spring 9 is inserted into the plunger 10 and grounded proximally on the rear case 2.2, and the plunger 10 is pressed against the rear case 2.2, compressing the drive spring 9. When the drive spring 9 has been suitably compressed, the plunger 10 is rotated such that the plunger boss 10.1 engages a bayonet slot 2.3 formed in the case 2. The drive spring 9 may then be allowed to slightly expand and lock the plunger boss 10.1 within the bayonet slot 2.3. The plunger 10 can only be released from the bayonet slot 2.3 by axial translation in the proximal direction P relative to the rear case 2.2 and rotation relative to the rear case 2.2.

In an exemplary embodiment of a process for assembling the autoinjector 1, the shroud spring 8 is inserted into the front case 2.1 and grounded proximally in the front case 2.1, and the needle shroud 7 is pressed against the front case 2.1, compressing the shroud spring 9. A resilient shroud beam 7.1 on the needle shroud 7 contacts a compliant case backstop beam 2.4 on a syringe support portion 2.5 of the case 2. As the syringe 3 is not yet present in the case 2, the case backstop beam 2.4 is able to deflect in a radially inwards direction and the shroud beam 7.1 can pass the case backstop beam 2.4 in the proximal direction P. The syringe 3 is assembled into the front case 2.1 from the proximal direction P to the distal direction D. In an exemplary embodiment, the syringe 3 may be inserted with the needle 4 and the protective needle sheath 5 attached. In another exemplary embodiment, the needle 4 and/or the protective needle sheath 5 may be assembled to the syringe 3 after insertion of the syringe 3 into the front case 2.1. When the syringe 3 is inserted into the front case 2.1, the case backstop beam 2.4 abuts the syringe 3 and, thus, cannot be deflected radially inward. Thus, in order to allow the shroud 7 to move in the distal direction D relative to the front case 2.1, the shroud backstop beam 7.1 must deflect radially outward around the case backstop beam 2.4.

In an exemplary embodiment of a process for assembling the autoinjector 1, the assembled rear case 2.2, with the plunger 10 and the drive spring 9, may be coupled to the front case 2.1 after insertion of the syringe 3. As the rear case 2.2 engages the front case 2.1, the plunger boss 10.1 contacts an angled rib 2.6 on the front case 2.1, which applies axial (in the proximal direction P) and rotational forces to the plunger boss 10.1. The axial and rotational force applied to the plunger boss 10.1, causes the plunger 10 to move proximally and rotationally relative to the rear case 2.2, partially disengaging the bayonet slot 2.3. However, a first shroud boss 7.2 on the needle shroud 7 abuts the plunger boss 10.1, and the angled rib 2.6 and the first shroud boss 7.2 prevent the plunger boss 10.1 from fully disengaging the bayonet slot 2.3. Under the biasing force of the shroud spring 8, a second shroud boss 7.4 abuts the plunger boss 10.1, thus limiting extension distally of the needle shroud 7 from the case 2.

In an exemplary embodiment, the plunger boss 10.1, the angled rib 2.6 and the first shroud boss 7.2 comprise a plunger release mechanism 12.

In an exemplary embodiment of a process for assembling the autoinjector 1, the cap 11 is coupled to the protective needle sheath 5 after insertion of the syringe 3. The cap 11 may be arranged to engage the protective needle sheath 5 by a barb, snap-fit, friction, hooks, etc. such that the protective needle sheath 5 is moved axially in the distal direction D as the cap 11 moves axially in the distal direction D. The cap 11 may engage the needle shroud 7 and/or the case 2.

Figure 2A:
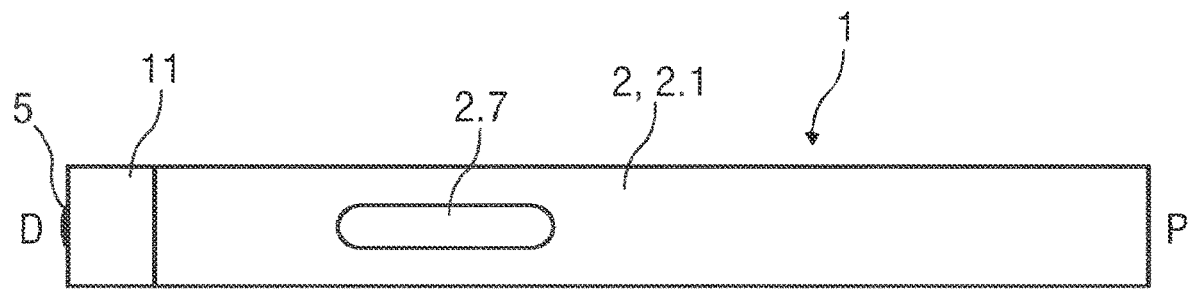
FIG. 2A is a side view of an exemplary embodiment of an autoinjector according to certain aspects of the present invention prior to use.
Figure 2B:
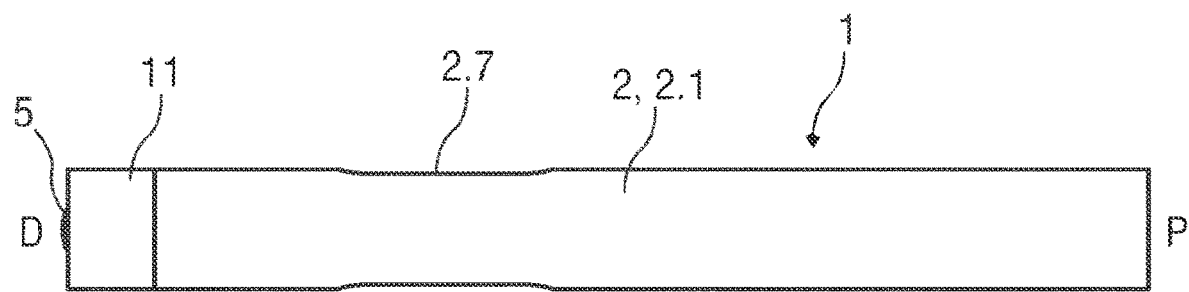
FIG. 2B is a different side view of an exemplary embodiment of an autoinjector according to certain aspects of the present invention prior to use.
Figure 2C:
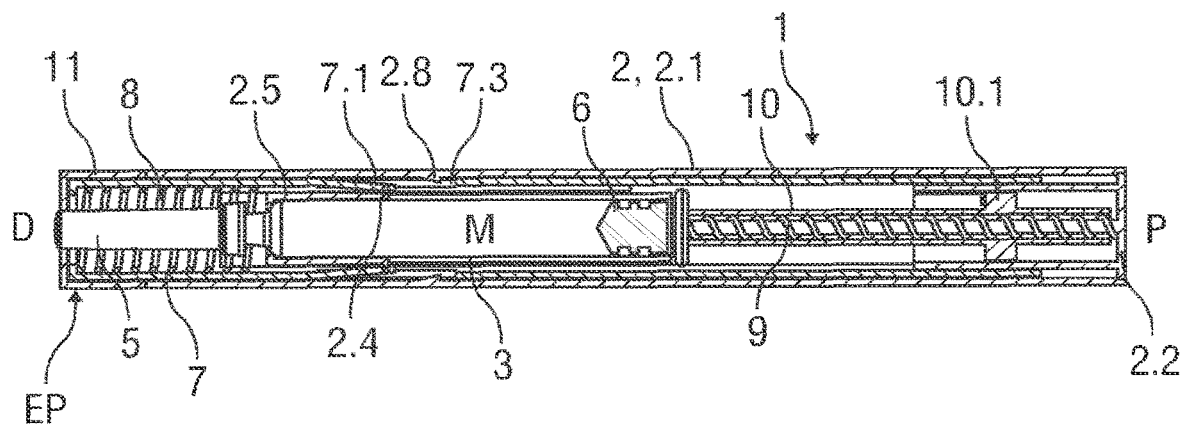
FIG. 2C is a longitudinal section of an exemplary embodiment of an autoinjector according to certain aspects of the present invention prior to use.
Figure 2D:
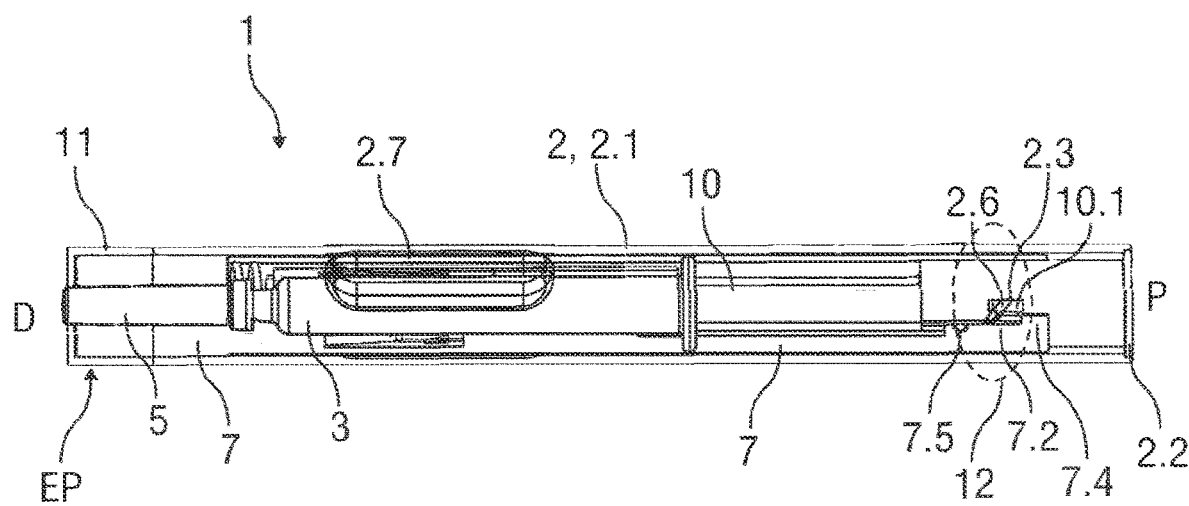
FIG. 2D is a semitransparent side view of an exemplary embodiment of an autoinjector according to certain aspects of the present invention prior to use.

FIGS. 2A and 2B are different side views of an exemplary embodiment of an assembled autoinjector 1 according to certain aspects of the present invention prior to use. FIG. 2C is a longitudinal section of an exemplary embodiment of an assembled autoinjector 1 according to certain aspects of the present invention. FIG. 2D is a semitransparent side view of an exemplary embodiment of an assembled autoinjector 1 according to certain aspects of the present invention.

A sequence of operation of an exemplary embodiment of an assembled autoinjector 1 according to certain aspects of the present invention may be as follows:

Prior to use, the autoinjector 1 is in the state as illustrated in FIGS. 2A to 2D. If applicable, the user removes the autoinjector 1 from the packaging. The user may then examine the medicament M through the viewing window 2.7.

The user removes the cap 11 pulling it in the distal direction D away from the case 2, thereby also removing the protective needle sheath 5. As the syringe 3 is held in the case 2, load exerted by pulling the cap 11 may be resolved by the case 2.

As shown in FIGS. 3A-3D, the needle shroud 7 is in an extended position EP protruding from the case 2 in the distal direction D. In an exemplary embodiment, the extended position EP is defined by the plunger boss 10.1 abutting the second shroud boss 7.4, thereby limiting movement of the needle shroud 7.4 relative to the case 2 in the distal direction D under the force of the shroud spring 8.

As shown in FIGS. 4A-4D, the autoinjector 1 is pressed against the injection site with the needle shroud 7 impacting the injection site and thereby moving the needle shroud 7 from the extended position EP to a retracted position RP against the bias of the shroud spring 8. As the needle shroud 7 translates from the extended position EP towards the retracted position RP, the plunger boss 10.1 rides along the first shroud boss 7.2. In an exemplary embodiment, the first shroud boss 7.2 may comprise a resistance element 7.5 which, when abutting the plunger boss 10.1, creates a tactile feedback of increased resistance against translation of the needle shroud 7 in the proximal direction P. The tactile feedback may indicate that needle insertion and/or delivery of the medicament M may commence with further depression of the needle shroud 7. Prior to the resistance element 7.5 bypassing the plunger boss 10.1, the autoinjector 1 may be removed from the injection site and repositioned as the needle shroud 7 will return to the extended position EP under the force of the shroud spring 8. Those of skill in the art will understand that in various exemplary embodiments, the resistance element 7.5 may include at least one of a bump, ramp, an abutment, a recess, spring detent, preloaded beam, etc.

Once the plunger boss 10.1 has passed the resistance element 7.5, the needle shroud 7 has sufficiently retracted such that the needle 4 is exposed and inserted into the injection site. Once the needle shroud 7 is fully depressed into the retracted position RP (and thus the needle 4 is fully inserted), the first shroud boss 7.2 is axially offset from and no long abutting the plunger boss 10.1.

As shown in FIGS. 5A-5D, under force of the drive spring 9, the plunger boss 10.1 rides the angled rib 2.6 in the distal direction D, rotating the plunger 10 relative to the case 2 and fully disengaging the bayonet slot 2.3. The plunger 10 is thus released and advances the stopper 6 in the distal direction D displacing the medicament M from the syringe 3 through the needle 4. In an exemplary embodiment, when the plunger 10 disengages the bayonet slot 2.3, the plunger boss 10.1 may impact the needle shroud 7 and generate an audible feedback indicating that delivery of the medicament M has been initiated. The advancing plunger 10 can be observed through the viewing window 2.7 to provide visual feedback about progress of the medicament delivery and indicate that the autoinjector 1 has been used.

As shown in FIGS. 6A-6D, when the autoinjector 1 is removed from the injection site, the needle shroud 7 moves from the retracted position RP towards a second extended position SEP driven by the shroud spring 8 to cover the needle 4. In the second extended position SEP, the needle shroud 7 protrudes further from the case 2 than in the extended position EP and is locked in an axial position relative to the case 2.

As the needle shroud 7 translates from the retracted position RP towards the second extended position SEP, the shroud beam 7.1 is deflected radially outwards around the case backstop beam 2.4. Once the shroud beam 7.1 has passed the case backstop beam 2.4, it returns to a non-deflected position radially inward. The needle shroud 7 cannot be translated in the proximal direction P relative to the case 2 from the second extended position SEP, because the shroud beam 7.1 will abut the case backstop beam 2.4, which is inwardly supported by the syringe 3 and can hence not deflect in the radially inward direction to allow the shroud beam 7.1 to pass. The needle shroud 7 is thus locked in the second extended position SEP. Further extension of the needle shroud 7 is prevented by a case boss 2.8 engaging with an end of a slot 7.3 in the needle shroud 7.

In an exemplary embodiment, if the autoinjector 1 is removed from the injection site prior to full medicament delivery, the needle shroud 7 will translate to the second extended position SEP. Hence, the risk of post-injection needle stick injury is reduced.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39), des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2,
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An autoinjector comprising:
   a case configured to hold a medicament container permanently axially fixed in the case against movement in a distal direction;
   a plunger movable in the distal direction relative to the case to dispense medicament from the medicament container; and
   a plunger release mechanism comprising:
      an angled surface;

a first shroud boss translatable between an extended position relative to the angled surface and a retracted position relative to the angled surface; and a plunger boss on the plunger, wherein the plunger boss is adapted to engage the angled surface such that the plunger boss rotates relative to the angled surface when the plunger boss is biased against the angled surface, wherein the first shroud boss is arranged to abut the plunger boss to inhibit the plunger boss from disengaging from the angled surface, and wherein the plunger boss is adapted to disengage from the angled surface when the first shroud boss is in the retracted position thereby axially misaligning the first shroud boss with the plunger boss such that the plunger boss, due to being biased in the distal direction towards the angled surface, rotates and comes clear of the angled surface to allow the plunger boss to translate axially relative to the angled surface.

2. The autoinjector according to claim 1, further comprising a second shroud boss proximal of the first shroud boss, wherein the second shroud boss is adapted to abut the plunger boss when the first shroud boss is in the extended position.

3. The autoinjector according to claim 1, further comprising a resistance element formed on the first shroud boss, wherein the resistance element is adapted to engage the plunger boss as the first shroud boss translates from the extended position to the retracted position.

4. The autoinjector according to claim 3, wherein the resistance element comprises at least one of a bump, a ramp, an abutment, a recess, a spring detent, or a preloaded beam.

5. The autoinjector according to claim 1, further comprising:
a backstop beam, and
a resilient shroud beam adapted to be deflected by the backstop beam when the first shroud boss translates from the retracted position to a second extended position distal to the extended position.

6. The autoinjector according to claim 5, wherein the resilient shroud beam is adapted to abut the backstop beam when the first shroud boss is in the second extended position to inhibit proximal movement of the first shroud boss.

7. The autoinjector according to claim 6, wherein the backstop beam is adapted to abut the medicament container when the first shroud boss is in the second extended position.

8. The autoinjector according to claim 1, wherein the first shroud boss is configured to be biased toward the extended position by a shroud spring.

9. The autoinjector according to claim 1, wherein the plunger boss is configured to be biased distally by a drive spring.

10. The autoinjector according to claim 1, further comprising a bayonet slot adapted to engage the plunger boss.

11. The autoinjector according to claim 10, wherein the plunger boss is adapted to partially disengage the bayonet slot when the plunger boss abuts the angled surface.

12. The autoinjector according to claim 1, wherein the angled surface is angled with respect to a longitudinal axis of the autoinjector and is configured to impart a rotational and an axial force on the plunger boss.

13. The autoinjector according to claim 1, further comprising a resistance element configured to abut the plunger boss to provide tactile feedback to a user as the first shroud boss translates from the extended position to the retracted position.

14. An autoinjector comprising:
a case configured to hold a medicament container permanently axially fixed in the case against movement in a distal direction;
a plunger movable in the distal direction relative to the case to dispense medicament from the medicament container; and
a plunger release mechanism comprising:
an angled surface;
a first shroud boss translatable between an extended position relative to the angled surface and a retracted position relative to the angled surface; and
a plunger boss adapted to engage the angled surface such that the plunger boss rotates relative to the angled surface when the plunger boss is biased against the angled surface,
wherein the plunger boss is adapted to disengage from the angled surface when the first shroud boss is in the retracted position thereby axially misaligning the first shroud boss with the plunger boss such that the plunger boss, due to being biased in the distal direction towards the angled surface, rotates and comes clear of the angled surface to allow the plunger boss to translate axially relative to the angled surface.

15. The autoinjector according to claim 14, further comprising:
a backstop beam, and
a resilient shroud beam adapted to be deflected by the backstop beam when the first shroud boss translates from the retracted position to a second extended position distal to the extended position.

16. The autoinjector according to claim 15, wherein the resilient shroud beam is adapted to abut the backstop beam when the first shroud boss is in the second extended position to inhibit proximal movement of the first shroud boss.

17. The autoinjector according to claim 16, wherein the backstop beam is adapted to abut the medicament container when the first shroud boss is in the second extended position.

18. The autoinjector according to claim 14, wherein the first shroud boss is configured to be biased toward the extended position by a shroud spring.

19. The autoinjector according to claim 14, further comprising a bayonet slot adapted to engage the plunger boss.

20. The autoinjector according to claim 19, wherein the plunger boss is adapted to partially disengage the bayonet slot when the plunger boss abuts the angled surface.

* * * * *